United States Patent
Snowden et al.

(10) Patent No.: US 6,787,184 B2
(45) Date of Patent: Sep. 7, 2004

(54) TREATED NONWOVEN FABRICS

(75) Inventors: Hue Scott Snowden, Woodstock, GA (US); Michael David Powers, Canton, GA (US); Steven Wayne Fitting, Acworth, GA (US); Varunesh Sharma, Atlanta, GA (US); Lee Kirby Jameson, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 92 days.

(21) Appl. No.: 10/007,375

(22) Filed: Dec. 5, 2001

(65) Prior Publication Data

US 2003/0045193 A1 Mar. 6, 2003

Related U.S. Application Data

(60) Provisional application No. 60/298,745, filed on Jun. 16, 2001.

(51) Int. Cl.$^7$ .................................................. B05D 1/36
(52) U.S. Cl. ...................... 427/209; 427/393.1; 427/412
(58) Field of Search ............................. 427/209, 393.1, 427/389.9, 412

(56) References Cited

U.S. PATENT DOCUMENTS

| | | | |
|---|---|---|---|
| 3,338,992 A | 8/1967 | Kinney ........................ 264/24 |
| 3,341,394 A | 9/1967 | Kinney ........................ 161/72 |
| 3,502,763 A | 3/1970 | Hartmann .................... 264/210 |
| 3,542,615 A | 11/1970 | Dobo et al. ................. 156/181 |
| 3,692,618 A | 9/1972 | Dorschner et al. ............ 161/72 |
| 3,769,060 A | 10/1973 | Ida et al. .................... 117/37 R |
| 3,802,817 A | 4/1974 | Matsuki et al. ............... 425/66 |
| 3,849,241 A | 11/1974 | Butin et al. .................. 161/169 |
| 3,855,046 A | 12/1974 | Hansen et al. ............... 161/150 |
| 3,899,615 A | 8/1975 | Wallsten ...................... 427/211 |
| 4,041,203 A | 8/1977 | Brock et al. ................. 428/157 |
| 4,082,887 A * | 4/1978 | Coates ........................ 442/114 |
| 4,340,563 A | 7/1982 | Appel et al. ................. 264/518 |
| 4,382,990 A * | 5/1983 | Coates ........................ 442/84 |
| 4,795,668 A | 1/1989 | Krueger et al. .............. 428/174 |
| 4,806,410 A | 2/1989 | Armington et al. ......... 428/126 |
| 5,008,178 A | 4/1991 | Van Thillo et al. ......... 430/527 |
| 5,057,368 A | 10/1991 | Largman et al. ............ 428/397 |
| 5,069,970 A | 12/1991 | Largman et al. ............ 428/373 |
| 5,078,154 A | 1/1992 | Patel et al. .................. 128/849 |
| 5,108,820 A | 4/1992 | Kaneko et al. .............. 428/198 |
| 5,145,727 A | 9/1992 | Potts et al. .................. 428/198 |
| 5,149,576 A * | 9/1992 | Potts et al. |
| 5,151,321 A * | 9/1992 | Reeves et al. |
| 5,169,706 A | 12/1992 | Collier, IV et al. ......... 428/152 |
| 5,178,931 A | 1/1993 | Perkins et al. .............. 428/198 |
| 5,178,932 A | 1/1993 | Perkins et al. .............. 428/198 |
| 5,188,885 A | 2/1993 | Timmons et al. ........... 428/198 |
| 5,277,976 A | 1/1994 | Hogle et al. ................. 428/397 |
| 5,336,552 A | 8/1994 | Strack et al. ................ 428/224 |
| 5,382,400 A | 1/1995 | Pike et al. ................... 264/168 |
| 5,466,410 A | 11/1995 | Hills ........................ 264/172.11 |
| 5,494,738 A | 2/1996 | Van Thillo et al. ......... 428/331 |
| 5,540,992 A | 7/1996 | Marcher et al. ............. 428/373 |

FOREIGN PATENT DOCUMENTS

| | | | |
|---|---|---|---|
| DE | 25 13 251 | 9/1976 | ............. D01F/8/08 |
| EP | 0 255 209 | * 2/1988 | |
| EP | 0 546 580 | 10/1996 | ............. D04H/1/64 |
| EP | 0 860 530 | * 8/1998 | |
| JP | 74-041513 | 11/1974 | .......... D06M/15/66 |

OTHER PUBLICATIONS

JP 72–008,797 1972 Japan (Derwent Abstract).
RD 193,032 May 10, 1980 Anonymous (Derwent Abstract).

* cited by examiner

Primary Examiner—Katherine A. Bareford
(74) Attorney, Agent, or Firm—William D. Herrick (57) ABSTRACT

Described is an improved two-step process for treating lightweight nonwovens to impart single-sided anti-static and alcohol repellency properties while maintaining good barrier characteristics as measured by hydrostatic head values. The resulting nonwovens find particular uses as infection control product medical fabrics for sterilization wrap and surgical gowns, for example.

11 Claims, 4 Drawing Sheets

TREATED NONWOVEN FABRICS

This application claims priority from U.S. Provisional Application No. 60/298,745 filed Jun. 16, 2001 incorporated herein by reference in its entirety.

BACKGROUND OF THE INVENTION

The present invention relates to treatment of nonwoven fabrics to impart desired properties. In particular, the invention provides relatively lightweight nonwoven fabrics with unique properties on opposing surfaces obtained by separate steps in a highly efficient and effective process. The invention also relates to resulting nonwovens having, for example, one surface that is alcohol repellent and the other that has antistatic properties suitable for use in the manufacture of infection control medical products including surgical gowns and sterilization wrap. Such nonwoven fabrics may also have excellent barrier properties as measured by hydrostatic head.

The manufacture of nonwoven fabrics for diverse applications has become a highly developed technology. Well known methods include spunbonding, meltblowing, carding, airlaying, and others. It is not always possible, however, to produce by these methods a nonwoven fabric having all desired attributes for a given application. As a result, it is often necessary to treat nonwoven fabrics by various means to impart such properties. For example, for medical applications such as surgeon's gowns, barrier to alcohol and blood penetration and bacteria is essential, and antistatic properties are very important. Unfortunately, treatments for barrier properties using fluorocarbons, for example, and treatments for antistatic properties using salts are detrimental to each other which makes it necessary to apply excessive amounts of one or both of the treatments. U.S. Pat. No. 5,178,931 addresses this concern by providing separately treated layers in a multi-ply construction. For lightweight fabrics or single component fabrics this is not always a satisfactory solution to efficiently and effectively providing a two sided nonwoven. European patent 0 546 580 B1 describes a printing process for treating one side only of a hydrophobic nonwoven with a wetting agent resulting in a two sided fabric with hydrophilic and hydrophobic properties. There remains a need, however, particularly for lightweight nonwovens, for improved means and methods for imparting two-sided properties of alcohol repellency and/or antistatic characteristics while maintaining hydrostatic head, all with reduced treatment chemical requirements.

SUMMARY OF THE INVENTION

The present invention addresses the difficulties and problems discussed above by providing a two-step treatment process for treating lightweight nonwovens and preserving desired properties of alcohol repellency on one side and/or antistatic characteristics on the other side. The resulting treated nonwoven also has good hydrohead properties. In one embodiment the process involves a saturation treatment for alcohol repellency using a minimum treatment amount followed by a single side spraying of a light amount of antistatic treatment composition. In a second embodiment each side is treated separately with printing forming light spray applications using a minimum of treatment composition resulting in imparting alcohol repellency and/or antistatic characteristics primarily to the respective treated sides only. Other application means are also contemplated. In these preferred embodiments the nonwoven has a basis weight in the range of from about 17 gsm to about 135 gsm and ideally for many applications, in the range of from about 34 to about 88 gsm. The alcohol repellency treatment will generally add only about 0.05 gsm to about 0.41 gsm to the fabric weight and ideally for many applications, within the range of from about 0.10 gsm to about 0.26 gsm. Similarly, the antistatic treatment composition will add only about 0.017 gsm to about 1.08 gsm to the fabric weight and ideally for many applications, within the range of from about 0.068 gsm to about 0.44 gsm. Despite these low add-on amounts, the treated nonwoven will have antistatic properties of less than about 0.50 sec by static decay test (described below) and ideally for many applications less than about 0.05 sec and will also have alcohol repellency of at least 3 to about 70% isopropyl alcohol and ideally for many applications, at least about 3 at 80% isopropyl alcohol. The treated nonwoven will also have a hydrohead of at least about 50 mB and ideally for many applications, at least about 70 mB. The resulting nonwoven is suited for use particularly as infection control products like a medical fabric especially when starting with a spunbond, meltblown or spunbond/meltblown laminate of polymers selected from thermoplastic polymers including polyolefins such as polypropylene, polyethylene as well as copolymers including propylene or ethylene monomer units.

DETAILED DESCRIPTION OF THE INVENTION

Test Procedures

Hydrohead: A measure of the liquid barrier properties of a fabric is the hydrohead test. The hydrohead test determines the height of water (in centimeters) which the fabric will support before a predetermined amount of liquid passes through. A fabric with a higher hydrohead reading indicates it has a greater barrier to liquid penetration than a fabric with a lower hydrohead. The hydrohead test is performed according to Federal Test Standard 191A, Method 5514.

Alcohol: Alcohol repellency was tested according to the test procedure described as follows. In this test, a fabric's resistance to penetration by low surface energy fluids is determined by placing 0.1 ml of a specified percentage of isopropyl alcohol (IPA) solution on the surface of the fabric and leaving the specimen undisturbed for 5 minutes. The grading scale ranges from 0 to 5, with 0 indicating the IPA solution wets the fabric and 5 indicating maximum repellency. This procedure is a modification of INDA Standard Test No. IST 80.9-74 (R-82).

Resistance to Blood Penetration (RBP): The blood strikethrough or resistance to blood penetration of a fabric is a measure of the amount of blood which penetrates the fabric at a particular pressure. The blood strikethrough is performed by weighing a blotter placed next to the fabric before and after the test which consists of applying 1 pound per square inch gauge (psig) pressure to the side of the fabric away from the blotter, which side has blood thereon.

The pressure is ramped up over approximately 10 seconds and removed when it reaches 1 psig. The difference in the weight of the blotter before and after the test in grams represents the amount of blood which has penetrated the fabric.

Grab Tensile test: The grab tensile test is a measure of breaking strength and elongation or strain of a fabric when subjected to unidirectional stress. This test is known in the art and conforms to the specifications of Method 5100 of the Federal Test Methods Standard 191A. The results are expressed in pounds or grams to break and percent stretch before breakage. Higher numbers indicate a stronger, more stretchable fabric. The term "load" means the maximum load or force, expressed in units of weight, required to break or rupture the specimen in a tensile test. The term "total energy" means the total energy under a load versus elongation curve as expressed in weight-length units. The term "elongation" means the increase in length of a specimen during a tensile test. The grab tensile test uses two clamps, each having two jaws with each jaw having a facing in contact with the sample. The clamps hold the material in the same plane, usually vertically, separated by 3 inches (76 mm) and move apart at a specified rate of extension. Values for grab tensile strength and grab elongation are obtained using a sample size of 4 inches (102 mm) by 6 inches (152 mm), with a jaw facing size of 1 inch (25 mm) by 1 inch, and a constant rate of extension of 300 mm/min. The sample is wider than the clamp jaws to give results representative of effective strength of fibers in the clamped width combined with additional strength contributed by adjacent fibers in the fabric. The specimen is clamped in, for example, a Sintech 2 tester, available from the Sintech Corporation, 1001 Sheldon Dr., Cary, N.C. 27513, an Instron Model TM, available from the Instron Corporation, 2500 Washington St., Canton, Mass. 02021, or a Thwing-Albert Model INTELLECT II available from the Thwing-Albert Instrument Co., 10960 Dutton Rd., Phila., Pa. 19154. This closely simulates fabric stress conditions in actual use. Results are reported as an average of three specimens and may be performed with the specimen in the cross direction (CD) or the machine direction (MD).

Antistatic properties were measured according to INDA Standard Test 40.2-92.

Porosity results were obtained by Frazier Porosity tests, ASTM Standard D737 "Air Permeability of Textile Fabrics," also Method 5450 Federal Test Methods Standard No. 191A, except that the specimen size is 8 inches by 8 inches.

Definitions

As used herein and in the claims, the term "comprising" is inclusive or open-ended and does not exclude additional unrecited elements, compositional components, or method steps.

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns or an equivalent but more recognized term, micrometers. (Note that to convert from osy to gsm, multiply osy by 33.91). As used herein the term "spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 20 microns. The fibers may also have shapes such as those described in U.S. Pat. No. 5,277,976 to Hogle et al., U.S. Pat. No. 5,466,410 to Hills and U.S. Pat Nos. 5,069,970 and 5,057,368 to Largman et al., which describe fibers with unconventional shapes.

As used herein the term "meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers are microfibers which may be continuous or discontinuous, are generally smaller than 10 microns in average diameter, and are generally tacky when deposited onto a collecting surface.

As used herein "multilayer laminate" means a laminate wherein some of the layers are spunbond and some meltblown such as a spunbond/meltblown/spunbond (SMS) laminate and others as disclosed in U.S. Pat. No. 4,041,203 to Brock et al., U.S. Pat. No. 5,169,706 to Collier, et al, U.S. Pat. No. 5,145,727 to Potts et al., U.S. Pat. No. 5,178,931 to Perkins et al. and U.S. Pat. No. 5,188,885 to Timmons et al. Such a laminate may be made by sequentially depositing onto a moving forming belt first a spunbond fabric layer, then a meltblown fabric layer and last another spunbond layer and then bonding the laminate in a manner described below. Alternatively, the fabric layers may be made individually, collected in rolls, and combined in a separate bonding step. Such fabrics usually have a basis weight of from about 0.1 to 12 osy (3 to 400 gsm), or more particularly from about 0.75 to about 3 osy. Multilayer laminates may also have various numbers of meltblown layers or multiple spunbond layers in many different configurations and may include other materials like films (F) or coform materials, e.g. SMMS, SM, SFS, etc.

As used herein the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the molecule. These configurations include, but are not limited to isotactic, syndiotactic and random symmetries.

As used herein the term "conjugate fibers" refers to fibers which have been formed from at least two polymers extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement, a pie arrangement or an "islands-in-the-sea" arrangement. Conjugate fibers are taught in U.S. Pat. No. 5,108,820 to Kaneko et al., U.S. Pat. No. 4,795,668 to Krueger et al., U.S. Pat. No. 5,540,992 to Marcher et al. and U.S. Pat. No. 5,336,552 to Strack et al. Conjugate fibers are also taught in U.S. Pat. No. 5,382,400 to Pike et al. and may be used to produce crimp in the fibers by using the differential rates of expansion and contraction of the two (or more) polymers. Crimped fibers may also be produced by mechanical means and by the process of German Patent DT 25 13 251 A1. For two component fibers, the polymers may be present in ratios of 75/25, 50/50, 25/75 or any other desired ratios. The fibers may also have shapes such as those described in U.S. Pat. No. 5,277,976 to Hogle et al., U.S. Pat. No. 5,466,410 to Hills and U.S. Pat. Nos. 5,069,970 and 5,057,368 to Largman et al., which describe fibers with unconventional shapes.

As used herein "thermal point bonding" involves passing a fabric or web of fibers to be bonded between a heated calender roll and an anvil roll. The calender roll is usually, though not always, patterned in some way so that the entire fabric is not bonded across its entire surface, and the anvil roll is usually flat. As a result, various patterns for calender rolls have been developed for functional as well as aesthetic reasons. One example of a pattern has points and is the Hansen Pennings or "H&P" pattern with about a 30% bond area with about 200 bonds/square inch as taught in U.S. Pat. No. 3,855,046 to Hansen and Pennings. The H&P pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). The resulting pattern has a bonded area of about 29.5%. Another typical point bonding pattern is the expanded Hansen Pennings or "EHP" bond pattern which produces a 15% bond area with a square pin having a side dimension of 0.037 inches (0.94 mm), a pin spacing of 0.097 inches (2.464 mm) and a depth of 0.039 inches (0.991 mm). Another typical point bonding pattern designated "714" has square pin bonding areas wherein each pin has a side dimension of 0.023 inches, a spacing of 0.062 inches (1.575 mm) between pins, and a depth of bonding of 0.033 inches (0.838 mm). The resulting pattern has a bonded area of about 15%. Yet another common pattern is the C-Star pattern which has a bond area of about 16.9%. The C-Star pattern has a cross-directional bar or "corduroy" design interrupted by shooting stars. Other common patterns include a diamond pattern with repeating and slightly offset diamonds with about a 16% bond area and a wire weave pattern looking as the name suggests, e.g. like a window screen, with about a 19% bond area. Typically, the percent bonding area varies from around 10% to around 30% of the area of the fabric laminate web. As in well known in the art, the spot bonding holds the laminate layers together as well as imparts integrity to each individual layer by bonding filaments and/or fibers within each layer.

As used herein, the term "infection control product" means medically oriented items such as surgical gowns and drapes, face masks, head coverings like bouffant caps, surgical caps and hoods, footwear like shoe coverings, boot covers and slippers, wound dressings, bandages, sterilization wraps, wipers, garments like lab coats, coveralls, aprons and jackets, patient bedding, stretcher and bassinet sheets, and the like.

Composition percent amounts herein are expressed by weight unless otherwise indicated.

Figure 1:
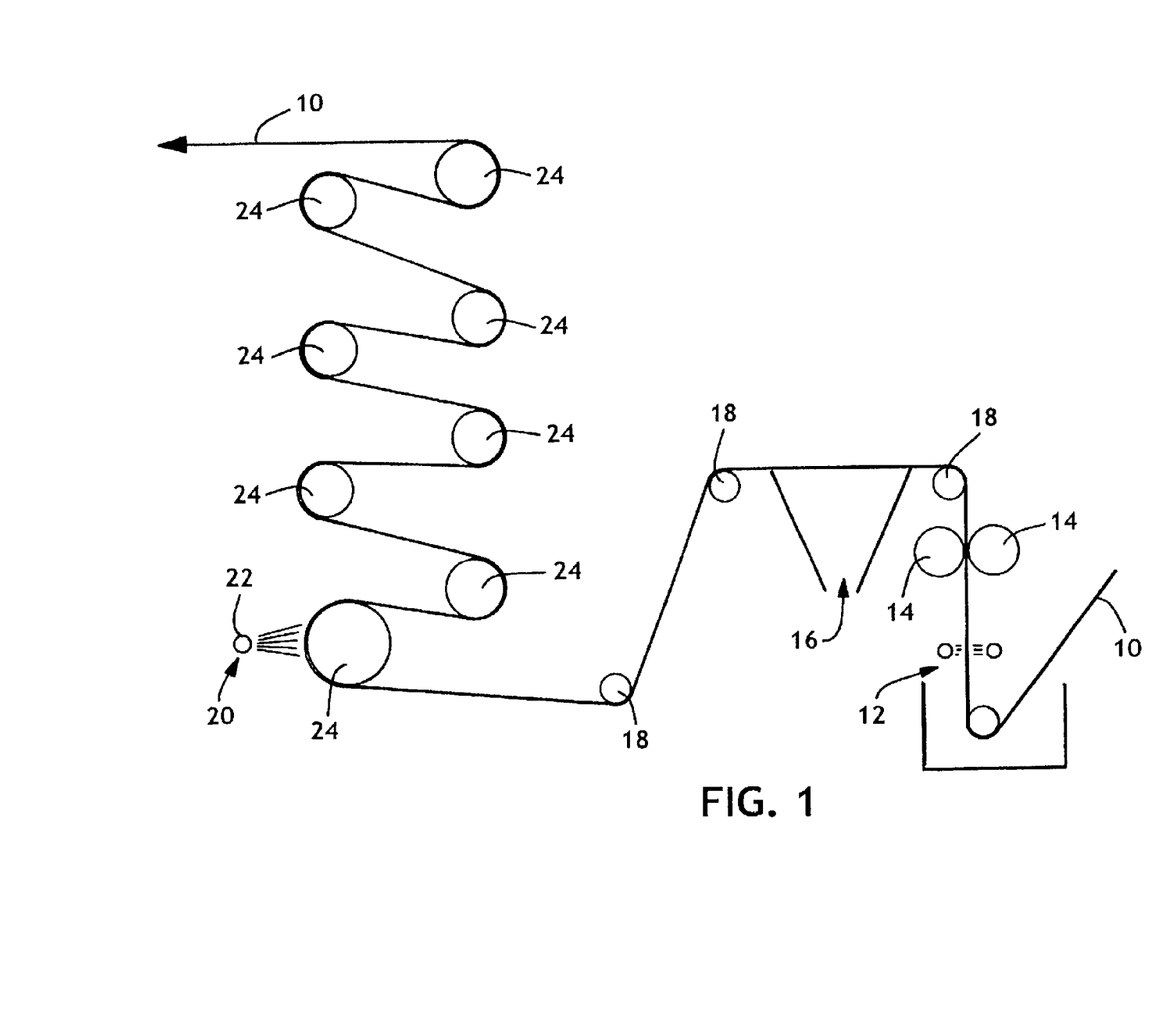
FIG. 1 is a schematic of one treatment process embodiment of the present invention using a saturation treatment step followed by a spray treatment step.

Turning to the drawings, FIG. 1 shows web 10 traveling from right to left. At saturation spray device 12 a fluorocarbon spray is applied to both sides. Squeeze nip rolls 14 remove excess fluorocarbon and vacuum extractor 16 removes additional treatment composition as web 10 travels over guide rolls 18. At treatment station 20 antistat is applied to one side only of web 10 by spray device 22 and at a point preferably prior to full curing of the fluorocarbon. Web 10 is then dried by contact with steam cans 24.

Figure 2:
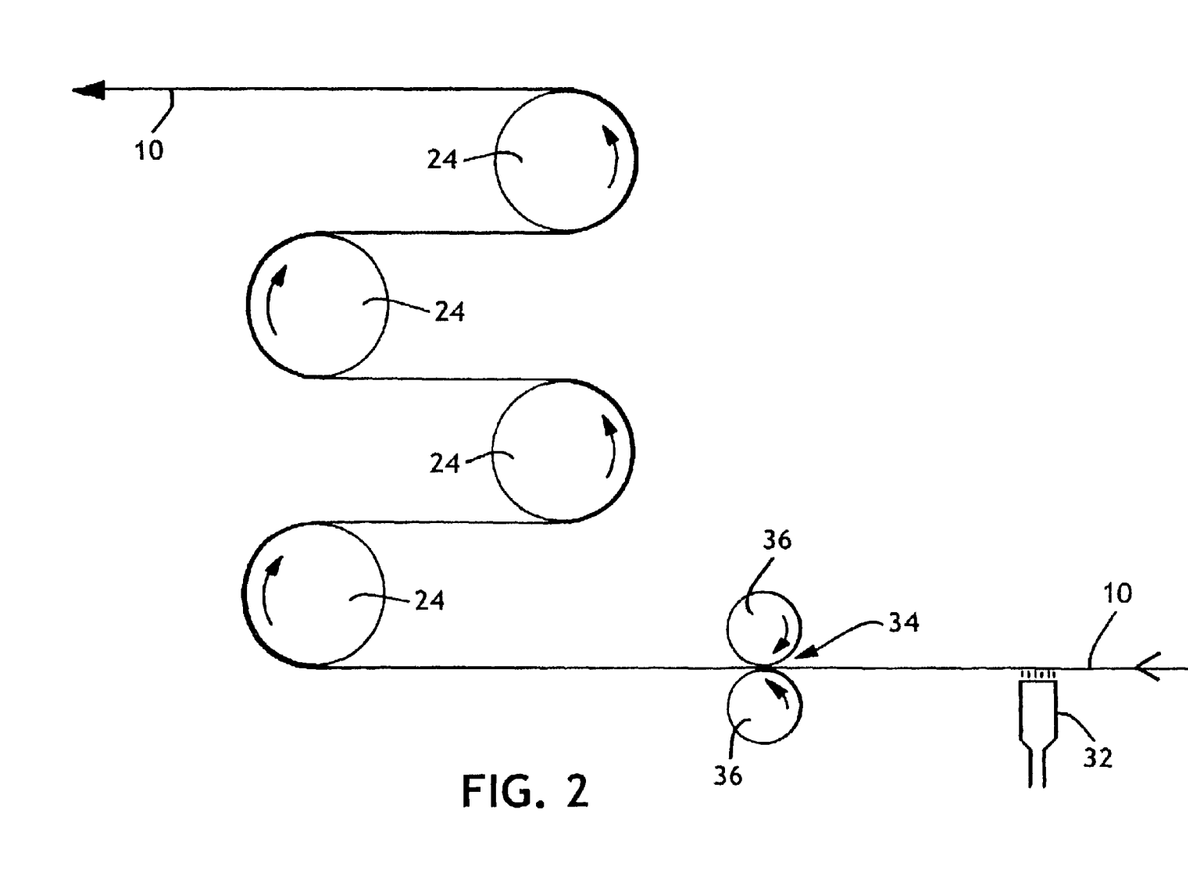
FIG. 2 is a schematic of a second treatment process embodiment of the present invention using a foam applicator instead of a spray treatment step.

FIG. 2 shows a process using a foam applicator to apply the fluorochemical instead of an antistatic spray device 22 as in FIG. 1. For FIG. 2, the system may be the same as FIG. 1 prior to the antistat spray 20 (FIG. 1) and is not shown. In FIG. 2, foam applicator 32 applies fluorocarbon composition as a foam. Excess is removed in the nip 34 between squeeze rolls 36, and web 10 is directed over steam cans 24 for drying as in FIG. 1.

Figure 3:
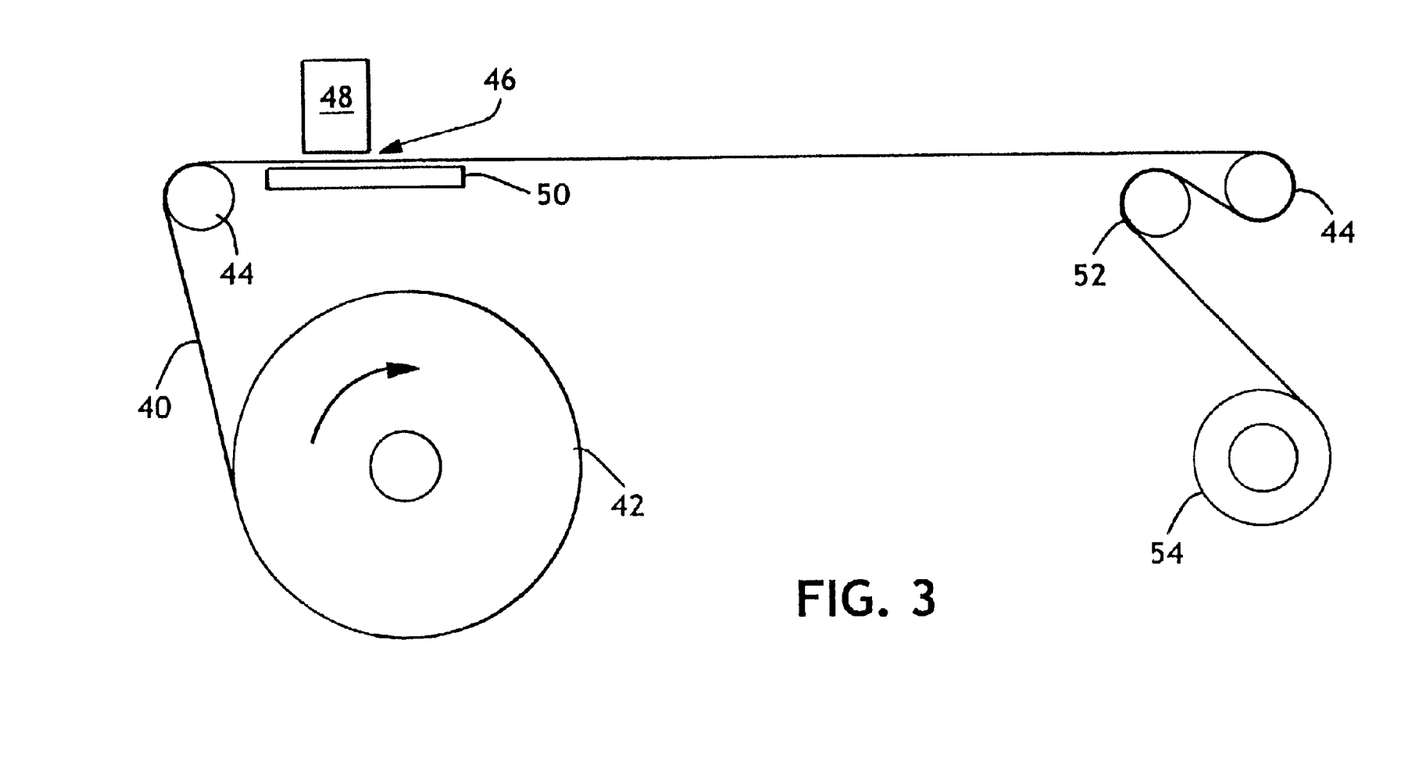
FIG. 3 is a schematic of the second step of the process of the invention using ink jet treating.

FIG. 3 shows schematically the second inline treatment step applied to web 40 having been previously treated as, for example, using the saturation spray device 12 of FIG. 1. In this embodiment web 40 is unwound from roll 42 and directed around guide roll 44 through printing station 46 including ink jet printhead 48 and web support platen/exhaust hood 50. The web has applied to the surface facing the printhead a light application of the antistat. The web may then be directed by one or more drive rolls 52 and rewound into treated roll 54 or, optionally, otherwise processed.

Figure 4:
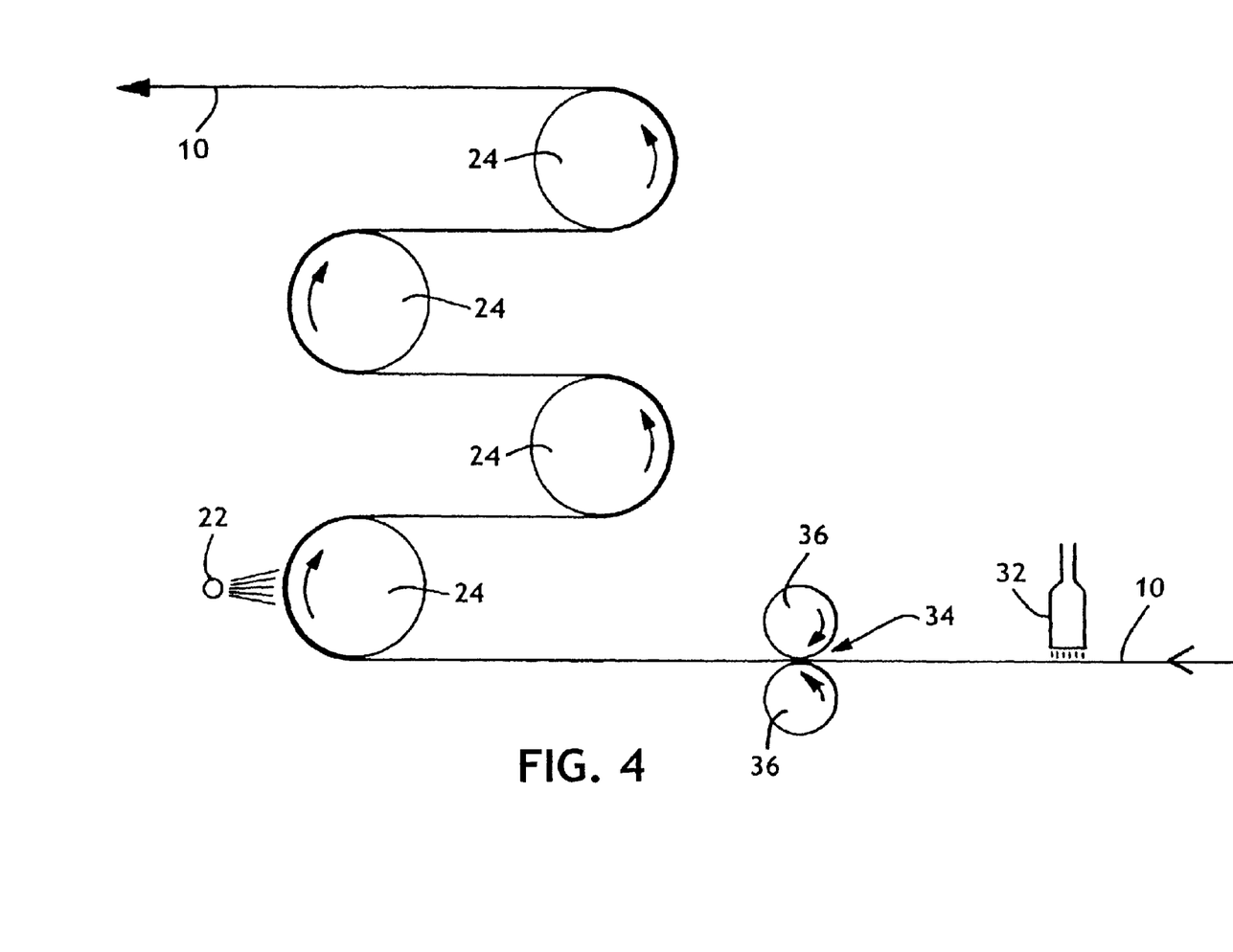
FIG. 4 is a schematic of a third treatment embodiment of the present invention applying antistat and repellent treatments to opposite sides.

FIG. 4 shows a third embodiment where the foam applicator 32 is used to apply fluorocarbon to one side of web 10 and spray 22 to apply antistat to the opposite side at steam can 24. Otherwise the process is like that of FIG. 2.

EXAMPLES

The present invention is further described by the examples which follow. Such examples, however, are not to be construed as limiting in any way either the spirit or the scope of the present invention.

For those examples using SMS fabric, the general process for forming the fabric and treating it was as follows:

A SMS (spunbond/meltblown/spunbond) laminate was formed all inline as described in U.S. Pat. No. 4,041,203 to Brock et al. After forming, the SMS laminate was thermally bonded with a bonding roll resulting in about 15% bond area in a wire weave pattern. The fabric produced had a basis weight of about 1.5 oz/yd2 (51 gsm) and was produced at about 760 ft/min. After bonding, the laminate was passed through a saturator where a partially fluorinated acrylic copolymer emulsion from DuPont (identified as Repellent 7700), and Zelec KC, an organic phosphate ester from Stepan Chemical, and a short chain alcohol (octanol) from Aldridge Chemical were applied as a mixture of about 2.85% in a ratio 2.5:0.1:0.25, respectively. The purpose of the fluorine containing compound is to give isopropanol repellency of 70% IPA or better to the finished, dried laminate. The amount in the bath was about 2.15% of the "as delivered" material. The purpose of the organic phosphate ester in this bath is to control the rate at which the fluorine containing material adheres to the fabric. The amount in the bath was about 0.05% of the "as delivered" material. The purpose of the alcohol is to aid in wetting out the laminate completely. As the water is dried off the laminate in a later step, the alcohol is volatilized also. The amount of octanol used was 0.25% of the chemical. After saturation, which results in about 300% wet pickup based on fabric weight, the fabric was run through a squeeze nip, resulting in a reduction in the wet pickup to about 100% and over a dewatering vacuum, apparatus, further reducing the wet pickup to about 40%. Next, additional organic phosphate ester was applied to one surface only of the fabric via an atomized spray apparatus resulting in an addition of about 0.05%, making the applied side of the fabric rich in phosphate ester antistatic agent on that surface, while the other surface had minimal phosphate ester. After drying using steam cans, the treated fabric was wound on cardboard cores.

Example 1

| Attribute | Average | Range | Minimum | Maximum | St Dev. |
|---|---|---|---|---|---|
| Bloods (RPB) % | 1.3 | 1.76 | 0.7 | 2.46 | 0.585 |
| Tensile (lbs.) | 15.49 | 5.7 | 11.9 | 17.6 | 1.568 |
| Hydrohead (mbar) | 71.09 | 30 | 57 | 87 | 7.711 |
| Porosity (cfm) | 37.1 | 6.5 | 34.2 | 40.7 | 2 |

Samples were tested for static decay and all had results of 0.01 sec. or less.
Control - Single Bath

| Attribute | Average | Range | Minimum | Maximum | St Dev. |
|---|---|---|---|---|---|
| Bloods (RPB) % | 1.25 | 2.54 | 0.49 | 3.03 | 0.647 |
| Tensile (lbs.) | 15.31 | 7.31 | 11.49 | 18.8 | 1.672 |
| Hydrohead (mbar) | 64.7 | 31.5 | 51.5 | 83 | 7.296 |
| Porosity (cfm) | 38.9 | 9.5 | 35.8 | 45.3 | 3.28 |

As shown, compared to the single bath control, hydrohead values are much improved in accordance with the invention.

Example 2
Sided Fluorochemical Atomized Spray Treatment

| Formulation: | |
|---|---|
| De-ionized Water | 474.15 g |
| Repellant 9356H | 24.6 g |
| 1-octanol | 1.25 g |

Procedure:

De-ionized water was used. Repellent 9356H is a fluorinated acrylic copolymer dispersion from DuPont. Its purpose is to give alcohol repellency to the dried fabric. 1-octanol (99%) was used as received from Aldrich Chemical Company, Inc. The purpose of the octanol is to aid in wetting of the fabric. This will volatilize with the water during the drying procedure. Materials were added in the order shown under vigorous agitation with Ross high shear mixer and allowed to mix for at least 15 minutes to fully solubilize octanol.

The nonwoven fabric to be treated was a three-layer laminate having a basis weight of 51 gsm, comprised of spunbond/meltblown/spunbond (SMS) polypropylene at 35%/30%/35% respectively. The spunbond layers were composed of 35 melt flow polypropylene while the meltblown was 800 melt flow polypropylene. The laminate was pattern bonded by the application of heat and pressure in a wireweave pattern as described above.

The dispersion was applied to one side of the SMS at 100% wet pick-up (% WPU) via a handheld spray gun, model DH7500 from Campbell Hausfeld. % WPU was determined by weighing the sample before and after drying. % WPU=100*(Weight Wet-Weight Dry)/Weight Dry. 100% WPU correlates to approximately 1.0% dry fluorochemical add-on. After spraying, the fabric was run through a squeeze nip at a pressure of ~25 PSI to ensure penetration into the first spunbond layer and dried in a laboratory oven for approximately 3 minutes at 95° C. to cure the fluoropolymer and remove moisture.

| IPA Repellency Results: | |
|---|---|
| Treated Side: | 5 @ 80% IPA, 3 @ 90% IPA |
| Untreated Side: | 5 @ 20% IPA, 0 @ 30% IPA |

The results indicate that the treated side of the fabric displayed significantly higher alcohol repellency. In accordance with the invention the treated side was repellent at IPA of a percentage difference of 60% higher than the untreated side.

Example 3

| Formulation: | |
|---|---|
| De-ionized Water | 14280 g |
| Unidyne S-1042 | 1680 g |
| 1-octanol | 40 g |

Procedure:

De-ionized water was used Unidyne S-1042 is an experimental, proprietary fluoroalkyl acrylate copolymer emulsion from Daikin America, Inc. Its purpose is to give alcohol repellency to the dried fabric. 1-octanol (99%) was used as received from Aldrich Chemical Company, Inc. The purpose of the octanol is to aid in wetting of the fabric. This will volatilize with the water during the drying procedure. Materials were added in the order shown under vigorous agitation with Ross high shear mixer and allowed to mix for at least 15 minutes to fully solubilize octanol.

The nonwoven fabric to be treated was a three-layer laminate as in Example 1 comprised of spunbond/meltblown/spunbond (SMS) polypropylene at 35%/30%/35% respectively. The spunbond layers were composed of 35 melt flow polypropylene while the meltblown was 800 melt flow polypropylene. The laminate was pattern bonded by the application of heat and pressure in a wireweave pattern as described above.

The dispersion was foamed onto one side of the SMS via a Gaston CFS-6 Latex Foam Generator equipped with a parabolic applicator at a wet pick-up level of approximately 45% WPU was determined by weighing the sample before and after drying. % WPU=100*(Weight Wet-Weight Dry)/Weight Dry. 100% WPU correlates to approximately 1.8% dry fluorochemical add-on The fabric was then run through a squeeze nip as in Example 1 to ensure penetration into the first spunbond layer and dried in excess across steam cans to cure the fluoropolymer and remove moisture.

Alcohol repellency was then tested according to test procedure described above. The results indicate that the treated side of the fabric displayed significantly higher alcohol repellency.

| IPA Repellency Results: | |
|---|---|
| Treated Side: | 5 @ 60% IPA, 3 @ 70% IPA |
| Untreated Side: | 3 @ 30% IPA, 0 @ 40% IPA |

In accordance with the invention the treated side was repellent at a percentage of IPA at least 30% higher than the untreated side.

Example 4

Sided Fluorochemical Foam Treatment

| Formulation: | |
|---|---|
| De-ionized Water | 14993.6 g |
| Unidyne TG-573 | 966.4 g |
| 1-octanol | 40.0 g |

Procedure:

De-ionized water was used. Unidyne TG-573 is a fluoroalkyl acrylate copolymer emulsion from Daikin America, Inc. Its purpose is to give alcohol repellency to the dried fabric. 1-octanol (99%) was used as received from Aldrich Chemical Company, Inc. The purpose of the octanol is to aid in wetting of the fabric. This will volatilize with the water during the drying procedure. Materials were added in the order shown under vigorous agitation with Ross high shear mixer and allowed to mix for at least 15 minutes to fully solubilize octanol.

The nonwoven fabric to be treated was a three-layer laminate as in the previous example comprised of spunbond/meltblown/spunbond (SMS) polypropylene at 35%/30%/35% respectively. The spunbond layers were composed of 35 melt flow polypropylene while the meltblown was 800 melt flow polypropylene. The laminate was pattern bonded by the application of heat and pressure.

The dispersion was foamed onto one side of the SMS via a Gaston CFS-6 Latex Foam Generator equipped with a parabolic applicator at a wet pick-up level of approximately 35%. % WPU was determined by weighing the sample before and after drying. % WPU=100*(Weight Wet-Weight Dry)/Weight Dry. 35% WPU correlates to approximately 0.7% dry fluorochemical add-on. The fabric was then run through a squeeze nip to ensure penetration into the first spunbond layer and dried in excess across steam cans to cure the fluoropolymer and remove moisture.

Alcohol repellency was then tested. The results indicate that the treated side of the fabric displayed significantly higher alcohol repellency.

| IPA Repellency Results: | |
|---|---|
| Treated Side: | 5 @ 50% IPA |
| Untreated Side: | 3 @ 30% IPA, 0 @ 40% IPA |

Example 5

| Formulation: | |
|---|---|
| De-ionized Water | 150 mL |
| Unidyne S-1042 | 5 mL |
| 1-octanol | 3 mL |

Procedure:

De-ionized water was used as obtained from on-site system. Unidyne S-1042 is an experimental, proprietary fluoroalkyl acrylate copolymer emulsion from Daikin America, Inc. Its purpose is to give alcohol repellency to the dried fabric. 1-octanol (99%) was used as received from Aldrich Chemical Company, Inc. The purpose of the octanol is to aid in wetting of the fabric. This will volatilize with the water during the drying procedure. Materials were added in the order shown under vigorous agitation with Ross high shear mixer and allowed to mix for at least 15 minutes to fully solubilize octanol.

The nonwoven fabric to be treated was a three-layer laminate comprised of spunbond/meltblown/spunbond (SMS) polypropylene at 35%/30%/35% respectively. The spunbond layers were composed of 35 melt flow polypropylene while the meltblown was 800 melt flow polypropylene. The laminate was pattern bonded by the application of heat and pressure using the wireweave pattern described above.

The dispersion was ink-jetted onto one side of the SMS via an 8" wide MARSH LCP/ML8 a inkjet system at approximately 50% wet pick-up (WPU). %WPU was determined by weighing the sample before and after drying. %WPU =100*(Weight Wet-Weight Dry)Weight. The swatches of fabric were dried on a flat screen dryer (Model F10, Noble & Wood Lab Mach. Co.).

Alcohol repellency was then tested. In this test, a fabric's resistance to penetration by low surface energy fluids is determined by placing 0.1 ml of a specified percentage of isopropyl alcohol (IPA) solution on the surface of the fabric and leaving the specimen undisturbed for 5 minutes. The grading scale ranges from 0 to 5, with 0 indicating the IPA solution wets the fabric and 5 indicating maximum repellency. For purposes of the present invention, a rating of at least 3 is needed to be considered repellent. This procedure is a modification of INDA Standard Test No. IST 80.9-74 (R-82). The results indicate that the treated side of the fabric displayed significantly higher alcohol repellency.

| IPA Repellency Results: | |
|---|---|
| Treated Side: | 5 @ 60% IPA, 5 @ 70% IPA |
| Untreated Side: | 3 @ 30% IPA, 0 @ 40% IPA |

In accordance with the invention the treated side was repellent to an IPA percentage at least 30% higher than the untreated side.

While the invention has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A process for producing a lightweight nonwoven fabric having opposing first and second surfaces, one of which is rich in antistatic agent and one of which has less antistatic agent, said fabric having good barrier properties as measured by a rating of at least 3 when measured with 70% isopropyl alcohol for alcohol repellency and less than about 0.50 seconds static decay test, comprising the steps of:

applying an alcohol repellency treatment containing an antistatic agent to a first or both of said surfaces, resulting in an alcohol treatment add-on level of about 0.05 gsm to about 0.41 gsm and in a separate step, applying an antistatic treatment containing an antistatic agent to the second surface only of said fabric resulting in an antistatic treatment add-on level of about 0.017 gsm to about 1.08 gsm, and providing an antistatic rich surface.

2. The process of claim 1 wherein said nonwoven fabric has a basis weight in the range of from about 34 gsm to about 88 gsm.

3. The process of claim 1 wherein said nonwoven fabric opposing surfaces have a difference in demonstrated alcohol repellency of at least about 30% when exposed to isopropyl alcohol of varying concentrations.

4. The process of claim 1 wherein said nonwoven fabric comprises a spunbond layer and a meltblown layer.

5. The process of claim 4 wherein said nonwoven fabric comprises a meltblown layer between two spunbond layers.

6. The process of claim 1 wherein said nonwoven fabric has a hydrostatic head of at least about 50 mB.

7. The process of claim 1 wherein the step of applying an antistatic treatment occurs prior to fully curing the alcohol repellency treatment.

8. The process of claim 7 wherein said nonwoven fabric opposing surfaces have a difference in demonstrated alcohol repellency of at least about 30% when exposed to isopropyl alcohol of varying concentrations.

9. The process of claim 7 wherein said nonwoven fabric comprises a spunbond layer and a meltblown layer.

10. The process of claim 9 wherein said nonwoven fabric has a hydrostatic head of at least about 50 mB.

11. The process of claim 7 wherein said nonwoven fabric has a hydrostatic head of at least about 50 mB.

* * * * *